United States Patent [19]

Hartenstein et al.

[11] 4,120,964
[45] Oct. 17, 1978

[54] APORPHINE DERIVATIVES

[75] Inventors: Johannes Hartenstein, Stegen-Wittental; Gerhard Satzinger, Denzlingen, both of Germany

[73] Assignee: Warner-Lambert Company, Morris Plains, N.J.

[21] Appl. No.: 800,492

[22] Filed: May 25, 1977

[30] Foreign Application Priority Data

Jun. 4, 1976 [DE] Fed. Rep. of Germany ....... 2625116

[51] Int. Cl.$^2$ ..................... A61K 31/47; C07D 217/24
[52] U.S. Cl. ............................... 424/258; 260/289 C; 260/289 A
[58] Field of Search ..................... 260/289 C; 424/258

[56] References Cited

U.S. PATENT DOCUMENTS 3,131,191  4/1964  Douglas et al. ................. 260/289 A

OTHER PUBLICATIONS

Shamma "The Isoquinolne Alkaloids", pp. 221–224, Academic Press, (1972).

*Primary Examiner*—Donald G. Daus
*Assistant Examiner*—W. B. Springer
*Attorney, Agent, or Firm*—Albert H. Graddis; Frank S. Chow; George M. Yahwak

[57] ABSTRACT

The present invention is concerned with new and novel 4-hydroxyaporphine derivatives and with the preparation thereof.

8 Claims, No Drawings

APORPHINE DERIVATIVES

The new 4-hydroxy-aporphine derivatives according to the present invention are compounds of the general formula:

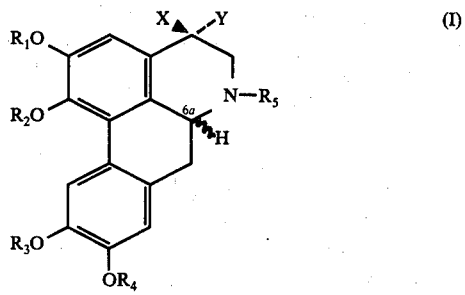

wherein $R_1$, $R_2$, $R_3$ and $R_4$, which may be the same or different, are methyl or ethyl radicals, $R_5$ Ol is a hydrogen atom or a straight-chained, cyclic or branched alkyl radical containing up to 5 carbon atoms and the symbol X or Y in the trans-position to the 6a hydrogen atom represents a hydroxyl group while the remaining X or Y symbol represents a hydrogen atom, with the proviso that when $R_5$ is a methyl radical, then at least one of the substituents $R_1$, $R_2$, $R_3$ or $R_4$ is an ethyl radical.

The pharmaceutically acceptable acid addition salts are also encompassed by this invention.

The wavy line in the 6a-position of the formula indicates an α-or β-bonding of the hydrogen atom. When the hydrogen atom has the α-configuration, then X is a hydroxyl group and Y is a hydrogen atom. When the hydrogen atom has the β-configuration, Y is a hydroxyl group and X is a hydrogen atom.

When $R_5$ is a straight-chained alkyl radical, it may be a methyl, ethyl, n-propyl, n-butyl or n-pentyl radical. Cyclic radicals include, for example, cycloalkylalkyl radicals, such as cyclopropylmethyl and cyclobutylmethyl radicals. Branched-chain alkyl radicals include, for example, isopropyl, isobutyl and isopentyl radicals.

Compounds of general formula (I) are preferred in which $R_1$, $R_2$, $R_3$ and/or $R_4$ is a methyl or ethyl radical and $R_5$ is a hydrogen atom or a methyl, ethyl or n-propyl radical.

Prior to our invention, only a limited number of compounds with the aporphine structure according to general formula (I) (with a hydroxyl group in the 4-position) have been described. Besides the naturally-occurring (+)-cataline ((+)-1-hydroxy-5-oxo-5H-pyrido[3,2a]phenoxazine-3-carboxylic acid) isolated from Glaucium flavum Cr. var. vestitum Tetrahedron Letters, p. 2033/1972), (+)-cataline has recently been synthesised by the oxidation of (+)-thaliporphine ((±)-5,6,6a,7-tetrahydro-2,9,10-trimethoxy-6-methyl-4H-dibenzo[de,g]quinolin-1-ol) with lead tetraacetate in acetic acid yielding (±)-4β-acetoxythaliporphine, which was then acid hydrolysed with hydrochloric acid at ambient temperature to give (±)-4β-hydroxythaliporphine which was, in turn, O-methylated with diazomethane (J.C.S. Chem. Comm., p. 306/1975).

Aporphine derivatives have also been prepared by the intramolecular, non-phenolic oxidative coupling of tetrahydroisoquinolines (J.A.C.S., 95, 6861/1973). However, prior to our invention, 4-hydroxy-aporphine derivatives have not been obtainable by this route. This coupling requires the cyclization of laudanosine in a solvent mixture of fluorosulphonic acid, methylene chloride and trifluoroacetic acid in a reaction solution of vanadyl trifluoride in trifluoroacetic acid. This process yields glaucine which is unsubstituted in the 4-position.

We have now found that the above-described reaction can be directed in such a manner that there is formed a 4-hydroxy-substituted aporphine derivative of general formula (I) or general formula (I') when, instead of the solvent mixture of methylene chloride and trifluoroacetic acid, there is used trifluoroacetic acid without the admixture of organic solvents.

This finding is extraordinarily surprising, since the hydroxylation effect according to our invention also involves a remarkably high regio- and stereo-selectivity. It is also surprising that hydroxyaporphines are exclusively formed which carry the hydroxyl function in the 4-position since the aporphine system contains three reactive benzylic positions. Since the 1-position of general formula II contains a more reactive hydrogen atom, it would be expected that a hydroxylation, if at all, would take place at this position, however, under the conditions of the process according to the present invention, the hydroxyl group enters preponderantly in the trans 4-position (referred to the 6a-hydrogen atom in general formula (I) or (I'). A further characteristic feature of the present invention is that the chiralic center in the tetrahydroisoquinoline (C-1) and in the aporphine ring system (C-6a) remains intact under the reaction conditions, i.e. that when using the optically-active tetrahydroisoquinolines of general formula (II), the corresponding optically-active 4-hydroxyaporphines of formula (I or (I') are obtained.

Consequently, the present invention also provides a process for the preparation of compounds of the general formula:

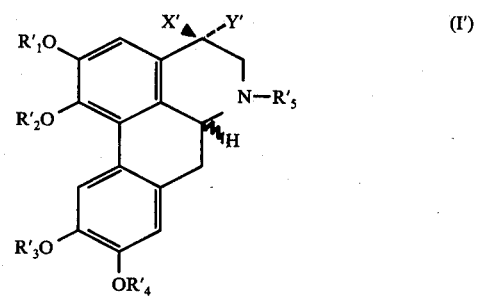

as well as of the salts thereof with organic and inorganic acids, wherein $R'_1$, $R'_2$, $R'_3$ and $R'_4$, which may be the same or different, are methyl or ethyl radicals and $R'_5$ is a hydrogen atom or a straight-chained, cyclic or branched alkyl radical containing up to 5 carbon atoms and the symbol X' or Y' in the trans-position to the 6a-hydrogen atom represents a hydroxyl group, while the remaining X' or Y' symbol represents a hydrogen atom, by the cyclisation of a compound of the general formula:

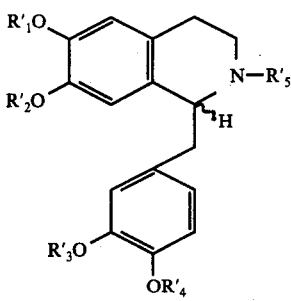

wherein $R'_1$, $R'_2$, $R'_3$, $R'_4$ and $R'_5$ have the same meanings as above, in trifluoroacetic acid, by reaction with vanadyl trifluoride. The reaction is carried out at a temperature of from −50° to +10° C, preferably from −15 to 0° C., without the admixture of an organic solvent. The vanadyl trifluoride used in a molar excess and water being subsequently added. The compound of general formula (I') is thus obtained and, if desired, converted into an acid addition salt.

As starting materials for the process according to the present invention, there can be used not only the racemic but also the enantiomeric compounds of general formula (II). Some of these starting materials are known for example, laudanosine (1-[(3,4-dimethoxyphenyl)methyl]-1,2,3,4-Tetrahydro-6,7-dimethoxy-2-methylisoquinoline) and N-ethyl- and N-propyltetrahydropapaverine. They are preferably prepared from the corresponding tetrahydroisoquinolines, for example tetrahydropapaverine, by alkylation (J. Chem. Soc., p. 1481/1962) or from the corresponding isoquinolines, for example, papaverine (1-[(3,4-dimethoxyphenyl)methyl]-6,7-dimethoxyisoquinoline) by alkylation and subsequent reduction, preferably by means of sodium borohydride (Ber. 90, 1997/1957).

For carrying out the reaction, the starting compounds of general formula (II) are dissolved, while cooling, in trifluoroacetic acid and mixed dropwise at −10° to −15° C with an excess amount of a vanadyl trifluoride trifluoroacetic acid solution, the reaction mixture becoming a red-violet color. It is generally preferable to use about a 2.5 mol excess of vanadyl fluoride per mol of tetrahydroisoquinoline to assure all the starting material is reacted.

After the addition of the vanadyl trifluoride solution, the reaction mixtue is further stirred for about 3 to 4 hours at −10° to −15° C and therafter allowed to rise to ambient temperature. After stirring for one hours at ambient temperature, the trifluoroacetic acid is removed in a vacuum and the residue, after being rendered alkaline, is partitioned between water and an organic solvent, for example, chloroform, methylene chloride or diethyl ether.

The 4-hydroxyaporphine may be obtained from the organic phase either by direct crystallization from an organic solvent or from an organic solvent mixture or after previous chromatographic separation on an insert carrier material, for example, silica gel or basic aluminium oxide by removal of the elution agent.

According to a preferred variant of the new process, the amount of expensive trifluoroacetic acid needed for the preparation of the vanadyl trifluoride solution (because of the poor solubility of vanadyl trifluoride in trifluoroacetic acid, relatively large volumes are necessary) is replaced by an inexpensive liquified sulphur dioxide. In this case, it is preferable to place the vanadyl trifluoride in liquified sulphur dioxide and to add dropwise a solution of the tetrahydroisoquinoline in trifluoroacetic acid at a temperature of from −15° to −50° C. Here, too, a coloration of the reaction mixture towards red-violet is observed. At the end of the dropwise addition, the reaction mixture is stirred for 4 − 5 hours at −10° to −15° C. The sulphur dioxide is then allowed to evaporate at ambient temperatures, the trifluoroacetic acid is removed in a vacuum and the residue treated as described above.

The salts of compounds of general formula (I) or (I') can be obtained by neutralization of the free bases with pharmacologically compatible inorganic or organic acids, for example, hydrochloric acid, sulphuric acid, phosphoric acid, hydrobromic acid, acetic acid, tartaric acid, lactic acid, citric acid, malic acid, salicylic acid, ascorbic acid, malonic acid, maleic acid or succinic acid.

The following examples are given for the purpose of illustrating the present invention:

EXAMPLE 1

(+)-4-Hydroxy-1,2,9,10-tetramethoxyaporphine

Variant A:

2 g. (±)-laudanosine is dissolved in 25 ml. trifluoroacetic acid and mixed dropwise at −15° C., while stirring and with the exclusion of moisture, with a solution of 1.73 g. vanadyl (V) fluoride in 50 ml. trifluoroacetic acid. The dark red solution obtained is stirred for a total of 4 hours at −15° C., then warmed to about 0° C. and the greater part of the trifluoroacetic acid removed under slightly reduced pressure. The residue is partitioned between water and chloroform. The organic phase is treated with an aqueous solution of ammonia and again washed with water. After drying in a vacuum, 2.1 g. of a yellow syrup remains. Either by direct crystallization (ethyl acetate/diethyl ether) or, after previous chromatography on silica gel or a basic aluminium oxide, there is obtained (±)-4-hydroxy-1,2,9,10-tetramethoxyaporphine; m.p. 152° − 153° C.

The corresponding acetate melts at 169° − 170° C.

NMR spectrum (60MHz, CDCl$_3$) δ 2.54 (s,3H,N-CH$_3$), 3.63 (s,3H,OCH$_3$), 3,90 (s,3H,OCH$_3$), 3.93 (s,6H,2OCH$_3$), 4.50 (m,1H,4-H), 6.77 (s,1H,ArH), 6.90 (s,1H,ArH),8.07 (s,1H,II-H).

Variant B:

0.93 g. vanadyl fluoride is suspended in about 60 ml. liquified sulphur dioxide. To the suspension is slowly added dropwise at −45° C. a solution of 1.07 g. (±)-laudanosine in 5 ml. trifluoroacetic acid; the reaction mixture becoming red-violet colored. After stirring for 2 hours at −45° C., a clear, deep red solution is obtained. This solution is stirred for an additional 4 hours at −15° C. By warming to ambient temperature, the sulphur dioxide is first evaporated off, followed by the trifluoroacetic acid under a vacuum. The residue is mixed with an aqueous solution of ammonia and extracted with chloroform. Further working up is then carried out as described in Variant A. Chromatography on silica gel with chloroform containing 0.1% triethylamine as elution agent gives 300 mg. (±)-4-hydroxy-1,2,9,10-tetramethoxyaporphine, as well as 300 mg. of the starting material, i.e. (±)-laudanosine.

EXAMPLE 2

(+)-4-Hydroxy-1.2.9.10-tetramethoxyaporphine (cataline) and
(−)-4-hydroxy-1,2,9,10-tetramethoxyaporphine 2 g. (+)-laudanosine (Eur. J. Med. Chem., 9, 237/1974) is reacted, in the manner described in Example 1, with 1.73 g. vanadyl (V) fluoride in trifluoroacetic acid. After analogous working up and crystallisation from diethyl ether, there is obtained (+)-4-hydroxy-1,2,9,10-tetramethoxyaporphine (cataline) in the form of colourless crystals; m.p. 180° - 182° C.;
$[\alpha]_D = +139.7$ (1.04 in chloroform).

Analysis:

$C_{21}H_{25}NO_5$

| | | | |
|---|---|---|---|
| calc.: | C 67.91%; | H 6.78%; | N 3.77% |
| found: | 68.16%; | 6.72%; | 3.55% |

UV: $\lambda_{max}^{EtOH}$ : 217 (30.500), 250 (sh 29.000), 272 (sh 12.000), 281 (14.500), 301 (13.600), 312 (sh 12.200) nm The corresponding acetate melts at 127° C., after recrystallisation from diethyl ether/petroleum ether.

In a corresponding manner, from (−)-laudanosine there is obtained the enantiomeric (−)-4-hydroxy-1,2,9,10-tetramethoxyaporphine, which melts at 179° -180° C.;
$[\alpha] = -147.7°$ (0.9 in chloroform).

Analysis:

$C_{21}H_{25}NO_5$

| | | | |
|---|---|---|---|
| calc.: | C 67.91%; | H 6.78%; | N 3.77% |
| found: | 67.56%; | 6.75%; | 3.59% |

UV: $\lambda_{max}^{EtOH}$ : 218 (39.300), 281 (14.500), 302 (13.600), 313 (12.100) nm

EXAMPLE 3

(±)-5,6,6a,7-Tetrahydro-1,2,9,10-tetraethoxy-6-methyl-4H-dibenzo[de,g]quinolin4-ol 2.31 g. (±)-diethoxy-1-(3',4'-diethoxybenzyl)-2-methyl-1,2,3,4-tetrahydroisoquinoline (Ber. 99, 2873/1966) is dissolved in 25 ml. trifluoroacetic acid and mixed dropwise at −15° C. with a solution of 1.73 g. vanadyl fluoride in 50 ml. trifluoroacetic acid. The red-violet solution obtained is stirred for 4 hours at −15° C. and for 1 hour at ambient temperature. The reaction mixture is evaporated in a vacuum, the residue mixed with ice water and 5% aqueous sodium bicarbonate solution and extracted with chloroform. The crude product obtained after drying and removing the solvent is chromatographed on silica gel with methylene chloride/methanol (99:1 v/v) and the eluate obtained is evaporated to give 657 mg. (±)-5,6,6a,7-tetrahydro-1,2,9,10-tetraethoxy-6-methyl-4H-dibenzo[de,g]quinoline, the hydrobromide of which, after recrystallisation from ethanol/diethyl ether, melts at 198° - 199° C., together with 721 mg. (±)-5,6,6a,7-tetrahydro-1,2,9,10-tetraethoxy-6-methyl-4H-dibenzo[de,g]quinolin-4-ol which, after recrystallisation from diethyl ether/petroleum ether, melts at 140° - 142° C. NMR spectrum (CDCl$_3$) δ 1.43 (m,12H,OCH$_2$CH$_3$), 2.47 (s,3H,N-CH$_3$),4.0 (m, -OCH$_2$CH$_3$), 4.42 (m,1H,4-H), 6.69 (s,1H,ArH), 6.80 (s,1H,ArH), 8.01 (s,1H,11-H).

EXAMPLE 4

(±)-5,6,6a,7-Tetrahydro-1,2,9,10-tetramethoxy-6-n-propyl-4H-dibenzo[de,g]quinolin-4-ol 11.95 g. (±)-1-(3,4-dimethoxybenzyl)-6,7-dimethoxy-2-n-propyl-1,2,3,4-tetrahydroisoquinoline (J. Chem. Soc., P. 1481/1962) is dissolved at 0° C. in 50 ml. trifluoroacetic acid. A solution of 9.6 g. vanadyl fluoride in 350 ml. trifluoroacetic acid is added dropwise, with stirring, to this solution at −15° C. After the addition, the reaction mixture is stirred for 2 hours at −15° C. and for 2 hours at ambient temperature. The reaction mixture is worked up in the manner described in Example 1 and direct crystallisation of the crude product from diethyl ether gives 2.6 g. (±)-5,6,6a,7-tetrahydro-1,2,9,10-tetramethoxy-6-n-propyl-4H-dibenzo[de,g]quinolin-4-ol, which melts at 153° - 154° C. By chromatography on basic aluminum oxide (activity stage III) with methylene chloride/petroleum ether (1:1 v/v) as elution agent, further amounts of thin layer chromatographically pure product are obtained. NMR spectrum (60 MHz, CDCl$_3$), δ 0.96 (m,3H,CH$_3$), 1.6 (m,2H), 3.65 (s,3H, OCH$_3$), 3.88 (s,9H,3xOCH$_3$), 4.44 (m,1H,4-H), 6.77 (s,1H, Ar-H), 6.95 (s,1H,ArH), 8.02 (s,1H,11-H).

EXAMPLE 5

(4S,6aS)-(+)-5,6,7a,7-Tetrahydro-1,2,9,10-tetramethoxy-6-n-propyl-4H-dibenzo[de,g]quinolin-4-ol 14.8 g. (+)-1-(3,4-dimethoxybenzyl-6,7-dimethoxy-2-n-propyl-1,2,3,4-tetrahydroisoquinoline (−)-dibenzoyl-tartrate is converted into the base by treatment with ammonia and extraction with chloroform. The solvent is removed in a vacuum and the residue taken up in 35 ml. trifluoroacetic acid. A solution of 6.38 g vanadyl fluoride in 250 ml. trifluoroacetic acid is added dropwise to this solution at −15° C., while stirring, in the course of 30 minutes. After completion of the addition, stirring is continued for 2 hours at −15° to −10° C. and for 2 hours at ambient temperature, followed by working up in the manner described in Example 1. Chromatography on basic aluminum oxide with methylene chloride/petroleum ether (1:1 v/v) and crystallization from diethyl ether gives (4S,6aS)-(+)-5,6,6a,7-tetrahydro-1,2,9,10-tetramethoxy-6-n-propyl-4H-dibenzo[de,g]quinolin-4-ol in the form of colorless crystals which melt at 152° - 153° C.; $[\alpha]_D = +132.5$ (0.5 in chloroform). NMR spectrum (60 MHz, CDCl$_3$), δ 1.0 (m,3H), 1.6 (m,2H), 3.64 (s,3H,OCH$_3$), 3.89 (s,9H,3xOCH$_3$), 4.44 (m,1H,4-H), 6.75 (s,1H, ArH), 6.83 (s,1H, Ar-H), 8.02 (s,1H,11-H).

The dextrarotary 1-(3,4-dimethoxybenzyl)-6,7-dimethoxy-2-n-propyl-1,2,3,4-tetrahydroisoquinoline used as starting material was obtained as follows from the racemic compound (J. Chem. Soc., P. 1481/1962); 16 g. of racemic hydrochloride was converted into the base by treatment with ammonia. Extraction with chloroform, drying and evaporating in a vacuum gives the base in the form of a viscous oil which is taken up in ethanol and mixed with 14.30 g. (−) dibenzoyl-tartaric acid. After seeding, the product is left to crystallize at ambient temperature. The crystals obtained are then recrystallized twice from hot isopropanol. The yield is 5 g. and the product melts at 155 -156° C.; $[\alpha]_C = +17.9$ (1in chloroform).

The base is liberated from the salt by treatment with dilute aqueous ammonia solution. Extraction with chloroform, drying, evaporation and subsequent recrystallization from aqueous ethanol gives crystalline (+)-1-)3,4-dimethoxybenzyl)-6,7-dimethoxy-2-n-propyl-1,2,3,4-tetrahydroisoquinoline, which melts at 78 – 80° C.; $[α]_d = +76.2°$ (1 in chloroform).

EXAMPLE 6

(4R, 6aR)-(-)-5,6,6a,7-Tetrahydro-1,2,9,10-tetramethoxy-6-n-propyl-4H-dibenzo[de,g]quinolin-4-ol.

11.35 g. (−)-(3,4-dimethoxybenzyl)-6,7-dimethoxy-2-n-propyl-1,2,3,4-tetrahydroisoquinoline (+)-dibenzoyl-tartrate is converted into the base by treatment with ammonia and extracted with chloroform. The base, after freeing from solvent and drying, is dissolved in 27 ml. trifluoroacetic acid and mixed, within the course of 30 minutes, at −15° C. with a solution of 4.89 g. vanadyl fluoride in 192 ml. trifluoroacetic acid. After further proceeding in a manner analogous to that described in Exaple 1, there is obtained, 5.02 g. of crude product which, for further purification, was chromatographed on 300 g. basic aluminum oxide (activity state III) with a mixture of petroleum ether/chloroform (85.15 v/v) as elution agent. The fractions containing the desired product are combined and evaporated in a vacuum and the residue is crystallized from diethyl ether. There is obtained (4R,6aR9-(−)-5,6,6a,7-tetrahydro-1,2,9,10-tetramethoxy-6-n-propyl-4H-dibenzo[de,g]quinolin-4-ol in the form of colorless crystals which melt at 151 – 153+ C.; $[α]_D = -142.4°$ (0.5 in chloroform). The NMR spectrum is identical with the spectrum of the enantiomeric compound (see Example 5).

Laevorotary 1-(3,4-dimethylbenzyl)-6,7-dimethoxy-2-n-propyl-1,2,3,4-tetrahydroisoquinoline was obtained, analogously to the preparation of the dextrarotary enantiomer, from the racemic compound (J. Chem. Soc., p. 1481/1962), as the D-dibenzoyl-tartrate, which melts at 154° – 155° C.; $[α]_D = -18.2°$ (1 in chloroform). From the dibenzoyl-tartrate, the free base is obtained by treatment analogous to that described in Example 5. The free base melts at 78 – 79° C.; $[α]_D = -77.1°$ (1in chloroform).

EXAMPLE 7

(±)-4-Hydroxy-1,2,9,10-tetramethoxy-N-noraporphine 2 g. (±)-Tetrahydropapaverine hydrochloride is converted into the base by treatment with semi-concentrated aqueous ammonia solution. It is extracted with chloroform, dried and the solvent removed in a vacuum. The residue is dissolved in 20 ml. trifluoroacetic acid and mixed dropwise at −15° C., while stirring, with a solution of 1.64 g. vanadyl fluoride in 100 ml. trifluoroacetic acid within the course of 15 minutes. The mixture becomes deep red colored. The reaction mixture is further stirred for 1 hours at −15° to −10° C. and for 4 hours at ambient temperature, followed by working up in the manner described in Example 1. The product obtained (2.11 g. of dark brown foam) is, for further purification, chromatographed on 100 g. basic aluminum oxide (activity stage III) with chloroform/triethylamine (99:1 v/v) as elution agent. Besides 500 mg. (±)-N-norglaucine (yellow foam; hydrobromide m.p. 252 – 253° C.), 720 mg. 4-hydroxy-N-norglaucine is obtained which, after recrystallization from diethyl ether, melts at 143° –146° C. NMR spectrum (60 MHz, $CDCl_3$) δ3.66 (s,3H, $OCH_3$), 3,92 (s,9H,3×$OCH_3$), 4.52 (m,1 H, 4-H), 6.73 (s, 1H, ArH), 6.89 (s1H, ArH), 8.10 (s1H,11-H).

The following compounds are prepared in an analogous manner:

(±)-5,6,6a,7-tetrahydro-1,2,9,10-tetramethoxy-6-isobutyl-4H-dibenzo[de,g]quinolin-4-ol;
(±)-5,6,6a,7-tetrahydro-1,2,9,10-tetraethoxy-6-n-pentyl-4H-dibenzo[de,g]quinolin-4-ol;
(±)-5,6,6a,7-tetrahydro-1,2,3,10-tetramethoxy-6-isopropyl-4H-dibenzo[de,g]quinolin-4ol;
(±)-5,6,6a,7-tetrahydro-1,2,9,10-tetramethoxy-6-cyclopropylmethyl-4H-dibenzo[de,g]quinolin-4-ol;
(±)-5,6,6a,7-tetrahydro-1,2-diethoxy-9,10-dimethoxy-6-cyclobutylmethyl-4H-dibenzo[de,g]quinolin-4-ol.

The preceding Examples are summarized in the following Table:

TABLE

| Position Example | (2) $R_1$ | (1) $R_2$ | (10) $R_3$ | (9) $R_4$ | (6) $R_5$ | + − |
|---|---|---|---|---|---|---|
| 1 | —$CH_3$ | —$CH_3$ | —$CH_3$ | —$CH_3$ | —$CH_3$ | (±) |
| 2 | —$CH_3$ | —$CH_3$ | —$CH_3$ | —$CH_3$ | —$CH_3$ | (+) (−) |
| 3 | —$CH_2$—$CH_3$ | —$CH_2$—$CH_3$ | —$CH_2$—$CH_3$ | —$CH_2$—$CH_3$ | —$CH_3$ | (±) |
| 4 | —$CH_3$ | —$CH_3$ | —$CH_3$ | —$CH_3$ | —$CH_2$—$CH_2$—$CH_3$ | (±) |
| 5 | —$CH_3$ | —$CH_3$ | —$CH_3$ | —$CH_3$ | —$CH_2$—$CH_2$—$CH_3$ | (+) |
| 6 | —$CH_3$ | —$CH_3$ | —$CH_3$ | —$CH_3$ | —$CH_2$—$CH_2$—$CH_3$ | (−) |
| 7 | —$CH_3$ | —$CH_3$ | —$CH_3$ | —$CH_3$ | H | |
| 8 | —$CH_3$ | —$CH_3$ | —$CH_3$ | —$CH_3$ | isobutyl | |
| 9 | —$CH_2$—$CH_3$ | —$CH_2$—$CH_3$ | —$CH_2$—$CH_3$ | —$CH_2$—$CH_3$ | n-pentyl | |
| 10 | —$CH_3$ | —$CH_3$ | —$CH_3$ | —$CH_3$ | isopropyl | |
| 11 | —$CH_3$ | —$CH_3$ | —$CH_3$ | —$CH_3$ | cyclopropyl-methyl | |
| 12 | —$CH_2$—$CH_3$ | —$CH_2$—$CH_3$ | —$CH_3$ | —$CH_3$ | cyclobutyl-methyl | |

Some of the 4-hydroxyaporphine of general formula (I) obtained by the process according to the present invention are valuable intermediates for the preparation of pharmacologically-effective products and some of them themselves possess interesting pharmacological properties. In particular, they have a remarkable action on the cardiovascular system.

Thus, they lower the blood pressure of hyper- and normotensive subjects. Therefore, those compounds not merely used as intermediates may also be used for the treatment of cardiovascular diseases which are to be attributed to hypertension.

The compounds of general formula (I) according to the present invention can be administered orally or parenterally in liquid or solid form. As injection solution, it is especially preferred to use water which contains the additives usual in the case of injection solutions, such as stabilizing agents, solubilizing agents or buffers.

Additives of this type include, for example, tartrate and citrate buffers, ethanol, complex-forming agents (such as ethylenediamine - tetraacetic acid and the non-toxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acid, high molecular weight fatty acids (such as stearic acid), gelatine, agar,agar, calcium phosphate, magnesium stearate, animal and vegetable fats and solid high molecular weight polymers (such as polyethylene glycols); compositions suitable for oral administration can, if desired, contain flavoring and/or sweeting agents.

Thus, the present invention also provides pharmaceutical compositions containing at least one of the new compounds according to the present invention, in admixture with a solid or liquid pharmaceutical diluent or carrier.

We claim:

1. A compound of the formula:

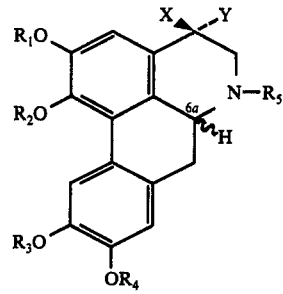

(I)

wherein $R_1$, $R_2$, $R_3$ and $R_4$ which may be the same or different are lower alkyls of 1 to 3 carbon atoms; $R_5$ is hydrogen or a straight chained, cyclic or branched lower alkyl of up to 5 carbon atoms; and wherein X or Y in the trans position to the 6α-hydrogen atom is hydroxyl while the remaining X or Y symbol is hydrogen; with the proviso that when $R_5$ is methyl then at least one of $R_1$, $R_2$, $R_3$ or $R_4$ is ethyl, and the pharmaceutically acceptable acid addition salts thereof.

2. A compound of claim 1 wherein $R_1$, $R_2$, $R_3$ and $R_4$ which may be the same or different is methyl or ethyl.

3. (±)-5,6,6a,7-Tetrahydro-1,2,9,10-tetraethoxy-6-methyl-4H-dibenzo[de,g]quinolin-4-ol.

4. (±)-5,6,6a,7-Tetrahydro-1,2,9,10-tetramethoxy-6-n-propyl-4H-dibenzo[de,g]quinolin-4-ol.

5. (4S,6aS)-(+)-5,6,6a,7-Tetrahydro-1,2,9,10-tetramethoxy-6-n-propyl-4H-dibenzo[de,g]quinolin-4-ol.

6. (4R,6aR)-(−)-5,6,6a,7-Tetrahydro-1,2,9,10-tetramethoxy-6-n-propyl-4H-dibenzo[de,g]quinolin-4-ol.

7. (±)-4-Hydroxy-1,2,9,10-tetramethoxy-N-norapor phine.

8. One compound according to "Phamaceutical compositions for the treatment of hypertension having an anti-hypertensive amount of a compound of claim 1, in admixture with a solid or liquid pharmaceutical diluent or carrier.

* * * * *